United States Patent [19]

Smith

[11] 3,981,931

[45] Sept. 21, 1976

[54] DIOLS BY TRANSESTERIFICATION USING MAGNESIA CATALYSTS

[75] Inventor: William E. Smith, Schenectady, N.Y.

[73] Assignee: General Electric Company, Pittsfield, Mass.

[22] Filed: Mar. 13, 1974

[21] Appl. No.: 450,587

[52] U.S. Cl. .......................... 260/635 R; 260/491; 260/497 A; 260/638 R
[51] Int. Cl.² .................. C07C 29/00; C07C 27/00
[58] Field of Search ............ 260/635 R, 638 R, 491, 260/497 A

[56] References Cited
UNITED STATES PATENTS

| | | |
|---|---|---|
| 2,388,164 | 10/1945 | Loder .............................. 260/491 |
| 2,578,647 | 12/1951 | Stiteler et al. ...................... 260/491 |
| 2,666,771 | 1/1954 | Zettlemoyer et al. ........... 260/638 R |
| 3,239,569 | 3/1966 | Slaugh et al. ...................... 260/491 |
| 3,328,439 | 6/1967 | Hamilton ...................... 260/638 R |
| 3,748,282 | 7/1973 | Evans................................ 423/155 |

OTHER PUBLICATIONS

Torraco and Turreziani, Chim., Ind. (Milan), 44, 483–488, (1962).

Primary Examiner—Joseph E. Evans
Attorney, Agent, or Firm—Donald M. Papuga; William F. Mufatti

[57] ABSTRACT

A process for preparing diols which comprises reacting diol esters with a lower alkanol in the presence of a transesterification catalyst comprising magnesia.

7 Claims, No Drawings

DIOLS BY TRANSESTERIFICATION USING MAGNESIA CATALYSTS

This invention relates to a process for preparing diols which comprises reacting diol esters with a lower alkanol in the presence of a transesterification catalyst comprising magnesia.

BACKGROUND OF THE INVENTION

There are several methods known in the art by which diol esters may be converted to the more useful diols. Aqueous base hydrolysis is unacceptable in that it involves the formation of salts, which must be further treated for recovery of their valuable components.

In copending applications of Will Dockery Merritt, Jr., Ser. No. 365,230 filed May 30, 1973, now abandoned, and John E. Corn et al, Ser. No. 365,239, filed May 30, 1973, now U.S. Pat. No. 3,880,939, assigned to the same assignee as this invention, processes involving alcoholysis of diol esters promoted by acidic ion exchange resins and alkali metal hydroxides, respectively, are disclosed. The liquid phase diol transesterification of dimethyl terephthalate and ethylene glycol promoted by magnesia (Torraco and Turreziani, Chim. Ind. (Milan), 44, 483–8 (1962) has also been described.

DESCRIPTION OF THE INVENTION

It has been discovered that diols may be produced with high efficiency by reaction of the corresponding diol esters with lower alkanols in the presence of a magnesia transesterification catalyst. The term "diol esters" refers to particular diol esters and mixtures of diol esters as well. The term is also meant to include both mono- and diester derivatives of diols.

The process is illustrated, for the case of preparation of 1,4-butanediol by methanolysis of 4-acetoxybutanol, in equation (1).

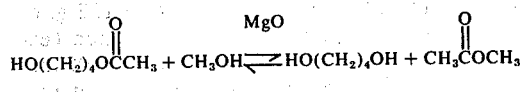

(1)

In addition to the advantages inherent in a stationary, heterogenous catalyst, the magnesia in this process is selective with respect to the transesterification reaction, and is not subject to destruction in side reactions.

The carboxylate moieties in these esters are those derived from the lower alkyl carboxylic acids, i.e., those having from one to six carbon atoms. A preferred class of esters is the acetates. The lower alkanol may be selected from those having one to six carbon atoms, with methanol a preferred alkanol.

The catalysts that may be employed in this invention are magnesia in its various forms generally, including magnesium oxide, magnesium hydroxide, mixtures of these two and their mixtures containing inert substances such as magnesium silicate. Magnesia compositions of the type described in U.S. Pat. No. 3,748,282 are particularly active in promoting the transesterification process. These catalysts are composed of magnesium oxide, magnesium hydroxide and a manganese oxide promoter. This patent is incorporated herein by reference.

The temperatures at which the process can be carried out vary widely. Temperatures ranging from about 100°C. to about 250°C. are generally adequate. Preferably, the reaction is carried out at temperatures of from about 125°C. to about 235°C. The maximum depends upon destruction of the reactants or products, dehydration and dehydroacyloxylation reactions occuring under too vigorous conditions.

Although only atmospheric pressure is normally required, it will be of course apparent to those skilled in the art that superatmospheric or subatmospheric pressure may be used where conditions so dictate.

There are several mechanically different ways of carrying out this invention. The transesterification may be done in the vapor phase, by passing a mixture of the diol ester and alkanol (the latter usually in substantial excess) through a heated bed of the catalyst. The effluent is distilled directly, affording the diol and alkyl ester products, in addition to the alkanol and unconverted diol ester, which are recycled to the reaction zone.

Alternatively, the invention may be practiced as a trickling phase process, wherein the diol ester is allowed to trickle down through a bed of the catalyst against a countercurrent of the alkanol vapor. With this method the reaction may be taken to completion in a single pass, driven by removal of the alkanol ester from the top of the reactor.

Both of these methods may be adapted to continuous operation, the trickling phase approach in particular.

Both methods are suitable for production of the butanediols from the butanediol esters as mentioned supra. Because of the basic nature of the catalyst, essentially no tetrahydrofuran is formed from the 1,4-butanediol or ester precursor, particularly with the trickling phase technique, which is generally performed at lower temperatures than the vapor phase method.

The process may be employed for the production of a wide variety of diols. It is particularly suitable for production of a mixture of 1,4-butanediol, 1,2-butanediol and 2-methyl-1,3-propanediol from a mixture of 4-acetoxybutanol, 2-methyl-3-acetoxypropanol and 2-acetoxybutanol and the corresponding diol and diacetate disproportionation products.

In copending application A, Ser. No. 365,228 of William E. Smith, filed May 30, 1973, now abandoned, and assigned to the same assignee as the present invention, there is disclosed and claimed a process for making butanediols by reacting propylene, oxygen and a carboxylic acid to produce an allyl carboxylate which is then hydroformylated to produce the mixture of the corresponding aldehydes. Hydrogenation of the mixture produces a mixture of the esters of the corresponding diols. These are then de-esterified to produce the desired butanediols. In copending application B, Ser. No. 365,231 of William E. Smith, filed May 30, 1973, now abandoned, and assigned to the same assignee as the present invention, there is disclosed and claimed a process wherein the hydrogenation is accomplished concurrently with the hydroformylation reaction. De-esterification of the diol ester mixture produces the desired butanediols which can be separated by distillation.

In copending application C, Ser. No. 439,276 of William E. Smith and R. John Gerhart, filed Feb. 4, 1974 and assigned to the same assignee as the present invention there is disclosed and claimed a process for preparing allyl acetate by reacting propylene, methyl acetate, water and oxygen in the presence of a catalyst system comprising on oxidation catalyst and an acidic co-catalyst. In copending application D, Ser. No. 439,275 of William E. Smith and R. John Gerhart, filed Feb. 4, 1974 and assigned to the same assignee as the present invention, there is disclosed and claimed a process for preparing allyl acetate by reacting propylene, a mixture of methyl acetate, water, acetic acid, and methanol and oxygen in the presence of a catalyst comprising a Group VIII noble metal or its salts, or its oxides, or mixtures thereof. In copending application E, Ser. No. 439,277 of William E. Smith and R. John Gerhart, filed Feb. 4, 1974 and assigned to the same assignee as the instant invention, there is disclosed and claimed a process for preparing allyl acetate by reacting propylene, a mixture of methyl acetate, water, acetic acid, and methanol and oxygen in the presence of a catalyst comprising a Group VIII noble metal, or its oxides, or mixtures thereof and an acidic co-catalyst. Applications A, B, C, D, and E are incorporated herein by reference.

Another aspect of the present invention is concerned with an improved overall process for the production of butanediol from propylene which takes advantage of the magnesia promoted methanolysis and is represented in equations 2 - 4:

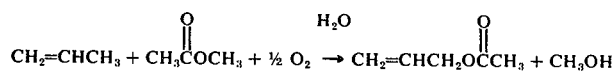

$$CH_2=CHCH_3 + CH_3\overset{O}{\overset{\|}{C}}OCH_3 + \tfrac{1}{2}\,O_2 \xrightarrow{H_2O} CH_2=CHCH_2O\overset{O}{\overset{\|}{C}}CH_3 + CH_3OH \quad (2)$$

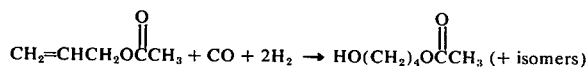

$$CH_2=CHCH_2O\overset{O}{\overset{\|}{C}}CH_3 + CO + 2H_2 \rightarrow HO(CH_2)_4O\overset{O}{\overset{\|}{C}}CH_3 \;(+\text{ isomers}) \quad (3)$$

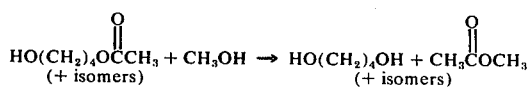

$$HO(CH_2)_4O\overset{O}{\overset{\|}{C}}CH_3 + CH_3OH \rightarrow HO(CH_2)_4OH + CH_3\overset{O}{\overset{\|}{C}}OCH_3 \quad (4)$$
(+ isomers)     (+ isomers)

The methyl acetate formed in the methanolysis reaction (equation 4) can be recycled to the hydrolysis-oxidation step (equation 2). Preferably, the methyl acetate is isolated and recycled as its azeotrope with methanol.

Specifically, the improved process for the production of butanediol comprises: (a) reacting propylene and a mixture of methyl acetate, water, acetic acid and methanol with oxygen in the presence of a catalyst comprising a Group VIII noble metal, or its salts, or its oxides, or mixtures thereof to form allyl acetate; (b) converting the allyl acetate under hydroformylation-hydrogenation conditions to a mixture comprising the monoacetate esters of 1,4-butanediol, 2-methyl-1,3-propanediol and 1,2-butanediol and their respective diol and diacetate disproportionation products; (c) de-esterifying the mixture of the acetate esters of the butanediols so produced with a lower alkanol in the presence of a transesterification catalyst comprising magnesia to produce the corresponding butanediols and methyl acetate; (d) isolating the methyl acetate from the butanediols in a form suitable for use in (a).

The process of forming allyl acetate in step (a) is fully set forth in copending application D, described above. The process of converting the allyl acetate under hydroformylation-hydrogenation conditions to a mixture comprising the monoacetate esters of 1,4-butanediol, 2-methyl-1,3-propanediol and 1,2-butanediol and their respective diol and diacetate disproportionation products, i.e., step (b) of the overall process of preparing 1,4-butanediol, is fully set forth in copending applications A and B described above.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE I

Apparatus — A vertical hot tube reactor (16mm ID × 70cm effective length) is constructed from heavy wall glass, with 24/40 male and female joints. Vigreaux points are indented just above the male joint to support catalyst pellets. Thermocouple leads are fastened into three other Vigreaux indentations at points along the length. Three 4 ft. × 1 in. Briskheat glass insulated heating tapes are wound onto the tube, covered with glass wool and glass tape, and connected to separate variable transformers. The tube exit is connected by a gooseneck (also heated) to an efficient condenser and collection vessel. A three-necked flask serves as the evaporator, with the reactants added from an addition funnel in a side neck. Nitrogen carrier gas is passed through to provide contact times on the order of 3 to 10 seconds.

The tube described above is charged with 152 g. of magnesia catalyst (Harshaw Mg 0601 T ⅛ inch (extruded pellets) ). After pretreatment with methanol vapor at 225°–250° C the tube is maintained at that temperature range while a mixture of 50 g of 1,4-butanediol diacetate and 75 ml of methanol is passed through over 1.5 hours. Analysis of the effluent by glpc indicates that about 80% of the diacetate is converted to monoacetate and diol, with production of the corresponding amount of methyl acetate. The volatiles are evaporated and the residue is combined with 75 ml fresh methanol and subjected to another pass through the tube. This process is repeated (total of five passes) until the conversion to butanediol is essentially complete. The product compositions as indicated by glpc after each pass are represented in Table I. Evaporation of the volatiles from the effluent of the final pass leaves 17.1 g of essentially pure 1,4-butanediol (66% yield).

When removed from the tube and examined, the catalyst appears to have undergone no surface degradation or change.

TABLE I

Vapor Phase Methanolysis of Butanediol Acetate.
Composition of Butanediol Derivatives in Effluent.

| Pass | Diacetate, % | Monoacetate, % | Diol, % |
|---|---|---|---|
| 0 | 100 | 0 | 0 |
| 1 | 22 | 42 | 36 |

TABLE I-continued

Vapor Phase Methanolysis of Butanediol Acetate. Composition of Butanediol Derivatives in Effluent.

| Pass | Diacetate, % | Monoacetate, % | Diol, % |
|------|--------------|----------------|---------|
| 2    | 6            | 29             | 65      |
| 3    | 1            | 11             | 88      |
| 4    | —            | 2              | 98      |
| 5    | —            | 1              | 99      |

EXAMPLE II

The tube described in Example I is modified to allow addition of the acetate from an addition funnel mounted on the top and is charged with 72.6 grams of "magnesia" catalyst (3/16 in. pills, manufactured by Dart Industries) containing about 45% magnesium hydroxide and 4% manganese oxide in addition to the magnesium oxide (50%). The reactor is maintained at 100°–150°C while 100 grams of crude butanediol monoacetate obtained from allyl acetate via the oxo process (containing, as determined by glpc analysis of a completely acetylated sample, 591 mmols of 1,4-butanediol derivatives, 47 mmols of 2-methyl-1,3-propanediol derivatives and 76 mmols of 1,2-butanediol derivatives) is dropped down over the catalyst against a countercurrent of 150 grams of methanol, over a 1.5 hour period. Methyl acetate and the excess methanol are condensed from the top effluent; the liquid that trickles into the boiler is rich in butanediol.

At completion of the pass, a reflux condenser is mounted above the tube; a small amount of methanol is refluxed to wash the catalyst.

The trickle phase is repeatly dropped over the hot catalyst (total of six passes), using methyl acetate-free methanol as the countercurrent phase. The final trickle phase contains, on removal of the methanol, 52.2 grams of butanediols, composed of 1,4-butanediol, 2-methyl-1,3-propanediol and 1,2-butanediol in 21 : 1 : 2 ratio. The 45.4 grams of 1,4-butanediol corresponds to a yield of 85% based on the amount of the 1,4-derivatives initially present.

EXAMPLE III

A mixture of 25 g of butanediol diacetate, 100 ml of methanol and 25 g of magnesia pellets is heated with a distilling head fitted to the system. The volatiles are distilled out and replaced with fresh methanol (400 ml) over a six hour period. Analysis of the supernate by glpc shows that all of the butanediol di- and monoacetate are converted to butanediol.

EXAMPLE IV

An 8 ft. × 1 inch diameter stainless steel tube is charged with one liter (1000 grams) of alumina catalyst (1/8 inch pellets, Harshaw AL-1802-E ⅛) and maintained at 250°C. while a mixture per hour of 910 grams of the methyl acetate-methanol azeotrope (composed of 740 grams of methyl acetate and 170 grams of methanol) and 900 grams of water is passed through under 80 psi pressure. The effluent contains, according to quantitative glpc analysis, 282 grams of acetic acid, 320 grams of methanol, 392 grams of methyl acetate, and 815 grams of water per hour. (The composition is essentially the same after a second pass, demonstrating that equilibrium has been reached). These results indicate that for equation 5, K = 0.2 under these conditions.

$$CH_3COCH_3 + H_2O \rightleftharpoons CH_3COH + CH_3OH \quad (5)$$

$$K = \frac{[CH_3COH][CH_3OH]}{[CH_3COCH_3][H_2O]} = 0.2$$

The hydrolysate is cooled to about 150°C. and mixed with (per hour) 2000 grams of propylene and 170 grams of oxygen. The resultant mixture is passed directly through a second 8 ft. × 1 inch diameter tube containing one liter of 4–8 mesh carbon impregnated with palladium (0.3%) and potassium acetate (3%), and operated at 160°C. and 80 psi pressure. The output per hour from this oxidation zone is a mixture (two liquid phases on cooling) composed of, according to quantitative glpc analysis, 355 grams of unconverted methyl acetate (48% recovery), 493 grams of allyl acetate (95% yield based on 52% conversion), 308 grams of methanol, a trace of acetic acid, and the excess water and propylene.

The mixture is distilled directly using a conventional distilling column. The methyl acetate and methanol are taken overhead, leaving the allyl acetate, water and a small amount of acetic acid as the bottoms products. Distillation of the overhead affords the methyl acetate-methanol azeotrope (suitable for direct recycle in allyl acetate production) and methanol (suitable for use in the butanediol acetate methanolysis to be described). The allyl acetate-water-acetic acid distillation residue is cooled; the upper phase, essentially pure allyl acetate, is decanted and used directly in the next stage of the process. The aqueous phase contains about 5% of the allyl acetate, which can be recovered by distillation.

A two liter stirred autoclave heated at 125°C. is pressurized with 3000 psi of 2:1 hydrogen/carbon monoxide and charged with a mixture of 400 grams of the allyl acetate, 8.0 grams of cobalt octacarbonyl and 400 ml. of benzene. An exothermic reaction and gas uptake ensue. After 15 minutes at 125°–145°C., the product mixture is pumped from the autoclave, cooled and vented. It is then decobalted by heating at 110°C. for 10 minutes in a closed vessel, the addition of acetic acid being unnecessary because of its presence as a decomposition product. (The cobaltous acetate which forms is filtered off and transformed to cobalt octacarbonyl by subjection to hydrogen/carbon monoxide at elevated temperature and pressure ([160°C., 3000 psi]). The benzene solution is concentrated and the products are flash distilled, affording 474 grams (91% yield) of oxo aldehydes containing minor amounts of the butanediol acetate compounds. A glpc analysis indicates the presence of 4-acetoxybutyraldehyde, 3-acetoxy-2-methyl-propionaldehyde and 2-acetoxybutyraldehyde in 7 : 1.5 : 1.5 ratio.

The aldehyde mixture is combined in a stirred autoclave with 50 grams of a 30% cobalt on silica catalyst, subjected to 1000 psi of hydrogen, and heated for 30 minutes at 150°C. Reduction to the diol derivatives is complete, in essentially quantitative yield.

After removal of the hydrogenation catalyst by filtration, the product mixture is examined by glpc and found to contain 4-acetoxybutanol, 3-acetoxy-2- methylpropanol and 2-acetoxybutanol, and small amounts of their respective diacetate and diol disproportionation products.

The low boiling components of the hydrogenation mixture (principally water, acetic acid and hydrogenation products derived from methacrolein and allyl acetate) are distilled off under reduced pressure. The residue is subjected to the magnesia - promoted methanolysis in a manner similar to that described in Example II. It is passed continuously down through an 8 ft. × 1 in. diameter tube packed with one liter of the catalyst described in Example II and maintained at 130°C, against a countercurrent of methanol vapor (2000 grams per 800 gram charge per hour). Methyl acetate and the excess methanol are condensed from the top effluent, and a butanediol-rich trickle phase is taken into the boiler. Analysis of the latter (in a case using a single charge) by quantitative glpc shows the presence of 248 g of 1.4 - butanediol (69% yield in the conversion from allyl acetate), 17 grams of 2-methyl-1,3-propanediol (5% yield), and 47 grams of 1,2-butanediol (13% yield).

Fractionation of the diols through a 4 ft. ×2 in. diameter Goodloe column affords the three isomers - 1,4-butanediol (bp 144°/20mm), 2-methyl-1,3-propanediol (bp 132°/20mm), and 1,2-butanediol (bp121°/20mm). Distillation of the other process components affords the methyl acetatemethanol azeotrope and methanol for recycle.

The overall process as described is operated semi-continuously to provide butanediol at about one pound per hour.

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A process for preparing diols which comprises reacting an alkane diol acetate with a lower alkanol in the presence of a transesterification catalyst selected from the group consisting of mixtures of magnesium oxide and magnesium hydroxide and mixtures of magnesium oxide, magnesium hydroxide and manganese oxide at a temperature of from about 100°C to about 250°.

2. The process of claim 1 wherein the transesterification catalyst is a mixture of magnesium oxide, magnesium hydroxide and manganese oxide.

3. The process of claim 1 wherein the transesterification catalyst is a mixture of magnesium oxide and magnesium hydroxide.

4. The process of claim 1 wherein the alkane diol acetate comprises a mixture of 4-acetoxybutanol, 2-methyl-3-acetoxy-propanol and 2-acetoxybutanol.

5. The process of claim 1 wherein the lower alkanol is methanol.

6. An improved process for the production of butanediol which comprises:
    a. reacting propylene and a mixture of methyl acetate, water, acetic acid and methanol with oxygen in the presence of a catalyst comprising a Group VIII noble metal, or its salts, or its oxides or mixtures thereof;
    b. converting the allyl acetate under hydroformylation-hydrogenation conditions to a mixture comprising the monoacetate esters of 1,4-butanediol, 2-methyl-1,3-propanediol and 1,2-butanediol and their respective diol and diacetate disproportionation products;
    c. de-esterifying the mixture of the acetate esters of the butanediols so produced with methanol in the presence of a transesterification catalyst selected from the group consisting of mixtures of magnesium oxide and magnesium hydroxide and mixtures of magnesium oxide, magnesium hydroxide and manganese oxide at a temperature of from about 100°C to about 250°C to produce the corresponding butanediols and methyl acetate;
    d. isolating the methyl acetate from the butanediols in a form suitable for use in (a).

7. The process of claim 6 wherein the transesterification catalyst is a mixture of magnesium oxide and magnesium hydroxide.

* * * * *